(12) United States Patent
Goklen et al.

(10) Patent No.: US 9,868,761 B2
(45) Date of Patent: *Jan. 16, 2018

(54) BUFFER SYSTEM FOR PROTEIN PURIFICATION

(71) Applicant: GlaxoSmithKline LLC, Wilmington, DE (US)

(72) Inventors: Kent E. Goklen, King of Prussia, PA (US); Eric J. Suda, Phoenixville, PA (US); Antonio Raul Ubiera, King of Prussia, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/450,106

(22) Filed: Mar. 6, 2017

(65) Prior Publication Data

US 2017/0174721 A1 Jun. 22, 2017

Related U.S. Application Data

(63) Continuation of application No. 14/007,689, filed as application No. PCT/US2012/031076 on Mar. 29, 2012, now Pat. No. 9,624,261.

(60) Provisional application No. 61/468,814, filed on Mar. 29, 2011.

(51) Int. Cl.
| | |
|---|---|
| *C07K 1/22* | (2006.01) |
| *B01D 15/38* | (2006.01) |
| *C07K 1/36* | (2006.01) |
| *B01D 15/18* | (2006.01) |
| *B01D 15/36* | (2006.01) |
| *B01D 15/42* | (2006.01) |

(52) U.S. Cl.
CPC ............ *C07K 1/22* (2013.01); *B01D 15/1871* (2013.01); *B01D 15/362* (2013.01); *B01D 15/363* (2013.01); *B01D 15/3809* (2013.01); *B01D 15/3847* (2013.01); *B01D 15/426* (2013.01); *C07K 1/36* (2013.01)

(58) Field of Classification Search
CPC ........ C07K 1/22; C07K 1/36; B01D 15/1871; B01D 15/362; B01D 15/363; B01D 15/3809; B01D 15/3847; B01D 15/426
See application file for complete search history.

(56) References Cited

U.S. PATENT DOCUMENTS

| | | | |
|---|---|---|---|
| 4,634,678 A | 1/1987 | Salstrom | |
| 9,624,261 B2 * | 4/2017 | Goklen | C07K 1/18 |
| 2003/0004094 A1 | 1/2003 | Ghose et al. | |
| 2006/0118492 A1 | 6/2006 | Shieh et al. | |
| 2008/0193981 A1 | 8/2008 | Fahrner et al. | |
| 2008/0207879 A1 | 8/2008 | Artur et al. | |
| 2009/0148435 A1 | 6/2009 | Lebreton et al. | |
| 2009/0280131 A1 | 11/2009 | DiPadova et al. | |
| 2009/0297620 A1 | 12/2009 | Kanehira | |
| 2010/0234577 A1 | 9/2010 | Mazzola et al. | |

FOREIGN PATENT DOCUMENTS

| | | |
|---|---|---|
| EP | 0 363 126 A | 4/1990 |
| EP | 0 617 049 B | 9/1999 |
| WO | WO 2006/138553 A2 | 12/2006 |
| WO | WO 2010/063717 A1 | 6/2010 |
| WO | WO 2010/127069 A1 | 11/2010 |

OTHER PUBLICATIONS

Bjorck and Kronvall, J. Immunol., 133:969 (1984)).
Bjorck, J. Immunol., 140:1194 (1988).
Butler, J. N., Ionic Equilibrium: Solubility and pH Calculations. John Wiley and Sons (1998).
Forsgren and Sjoquist, J. Immunol., 97:822 1966.
Ghose, S.; McNerney, T. M. Hubbard, B. pH transitions in ion-exchange systems: Role in the development of a cation exchange process for a recombinant protein. Biotechnol. Prog. 2002, 18, 530-537.
Mixed-mode Chromatography Selection Guide. http://www.pall.com/main/laboratory/literature-library-details.page?id=47502 May 30, 2012.
Ngo, et al., Kosmotropes Enhance the Yield of Antibody Purified by Affinity Chromatography using Immobilized Bacterial Immunoglobulin Binding Proteins, Journal ofImmunoassay&Immunochemistry, 29:105-115,2008.
Pabst, T.M., Carta, G. pH transitions in cation exchange chromatographic columns containing weak acid groups. (2007) Journal of Chromatography A, 1142, pp. 19-31.
Soto Perez, J. and Frey, D. D. Behavior of the Inadvertent pH Transient Formed by a Salt Gradient in the Ion-Exchange Chromatography of Proteins, Biotechnol. Prog. 2005, 21, 902-910.
Yu, et al., Purification of hCG Monoclonal Antibodies by rProtein A Affinity Chromatography, Chinese Journal of Pharmaceuticals 2010, 41(8).
Zhou, J. X., et al. pH—conductivity hybrid gradient cation-exchange chromatography for process-scale monoclonal antibody purification. Journal of Chromatography A, 1175 (2007) 69-80.

\* cited by examiner

*Primary Examiner* — Gary Counts
(74) *Attorney, Agent, or Firm* — Elizabeth J. Hecht; Edward R. Gimmi

(57) ABSTRACT

A method for purifying a protein using a simplified, sodium chloride-free buffer system that consists of two components (acid and base pairs) for appropriate solution pH control; and a third component for ionic strength control, where the third component is the sodium salt conjugate base.

18 Claims, 6 Drawing Sheets

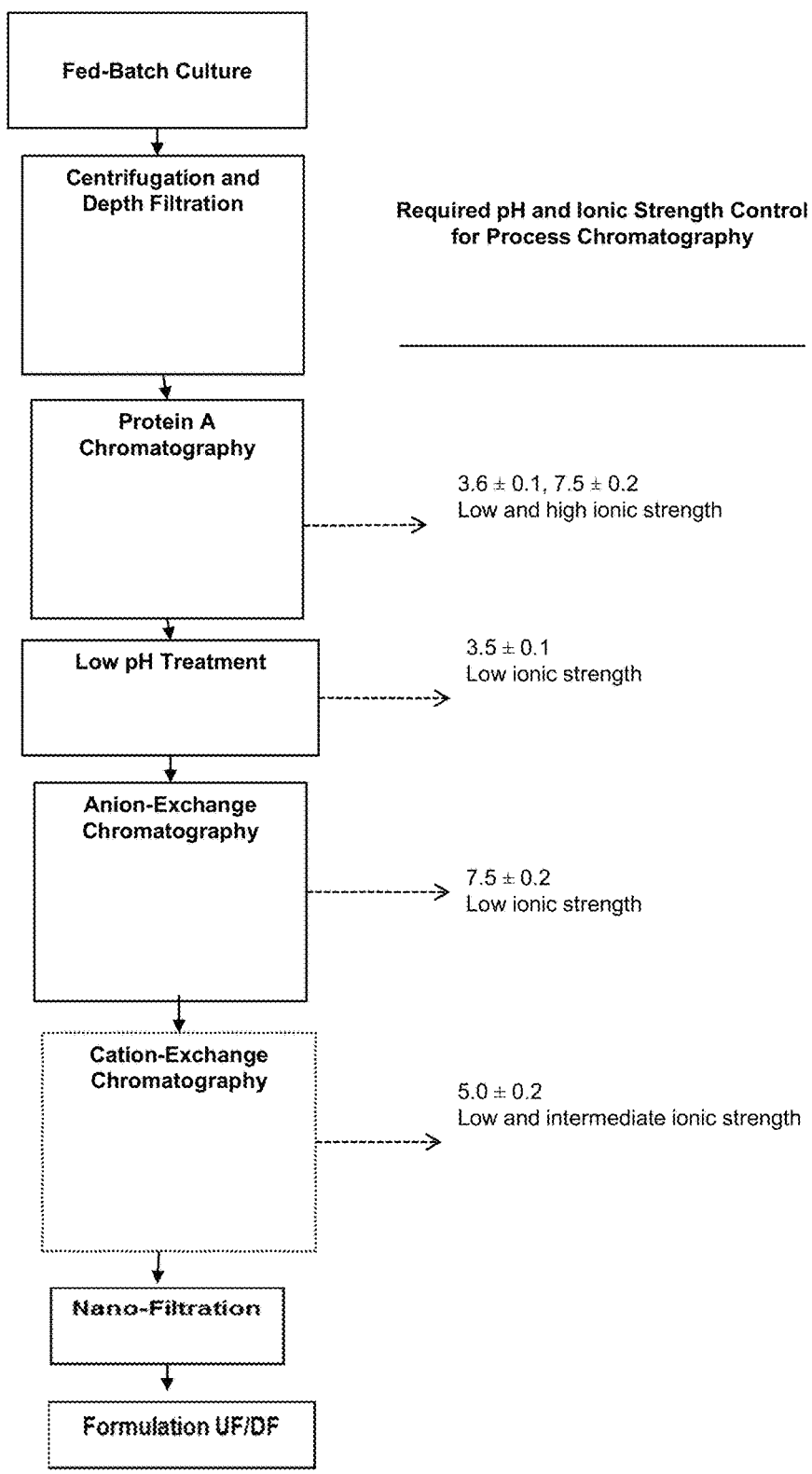
Figure 1. Downstream process flow diagram for mAb platform. Key pH and ionic strength ranges for process chromatography control are shown

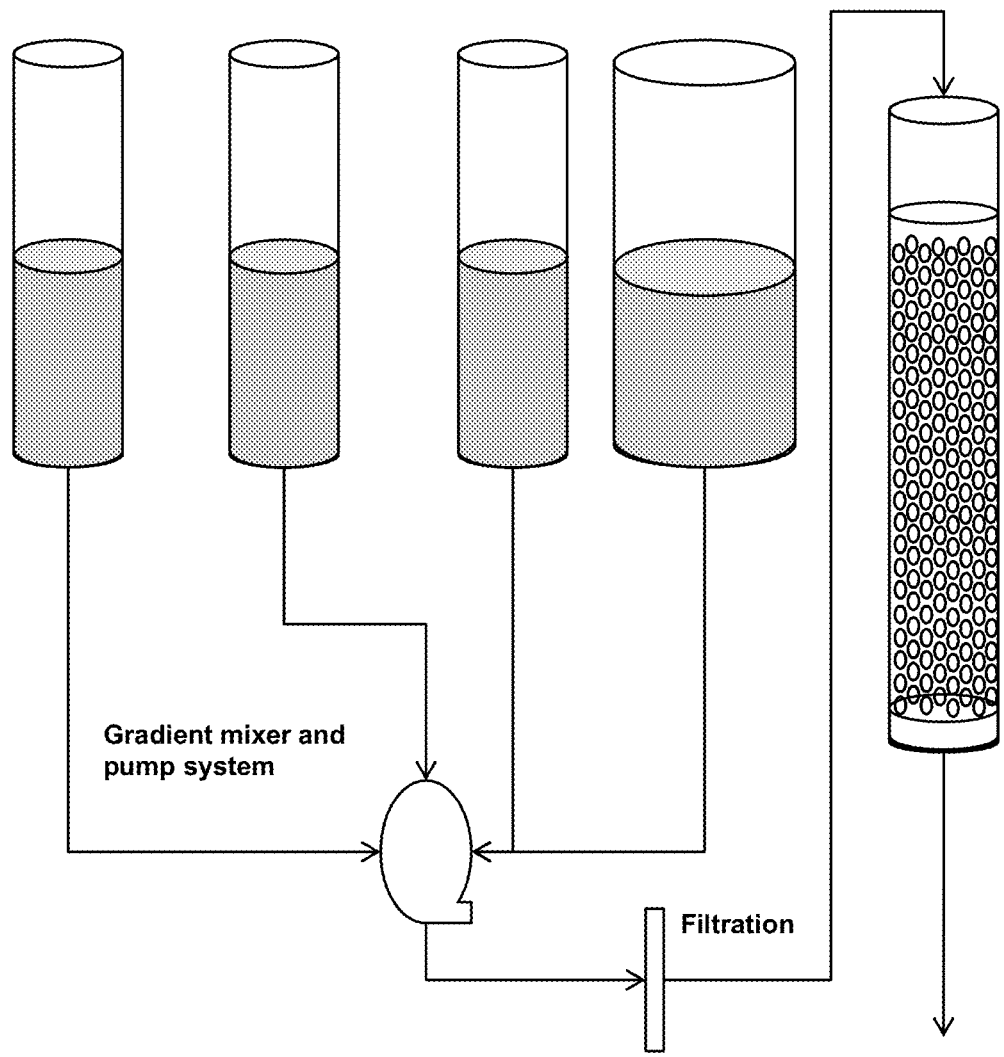
Figure 2. Diagram of ideal large scale buffer prep from concentrates for minimization of raw materials and tank requirements.

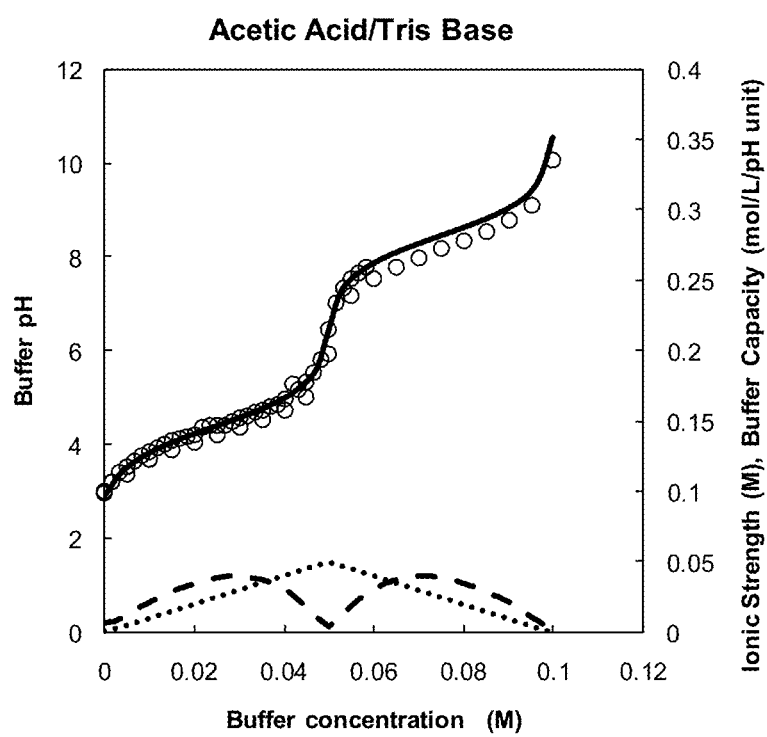
Figure 3. Calculated and experimental pH, ionic strength, and buffer capacity curves for acetic acid and tris base buffer system.

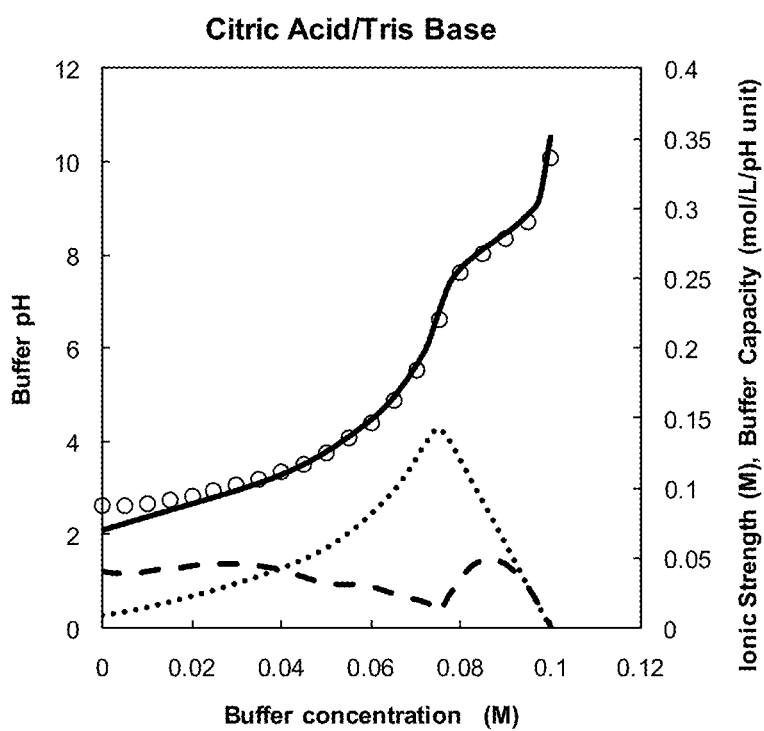
Figure 4. Calculated and experimental pH, ionic strength, and buffer capacity curves for citric acid and tris base buffer system.

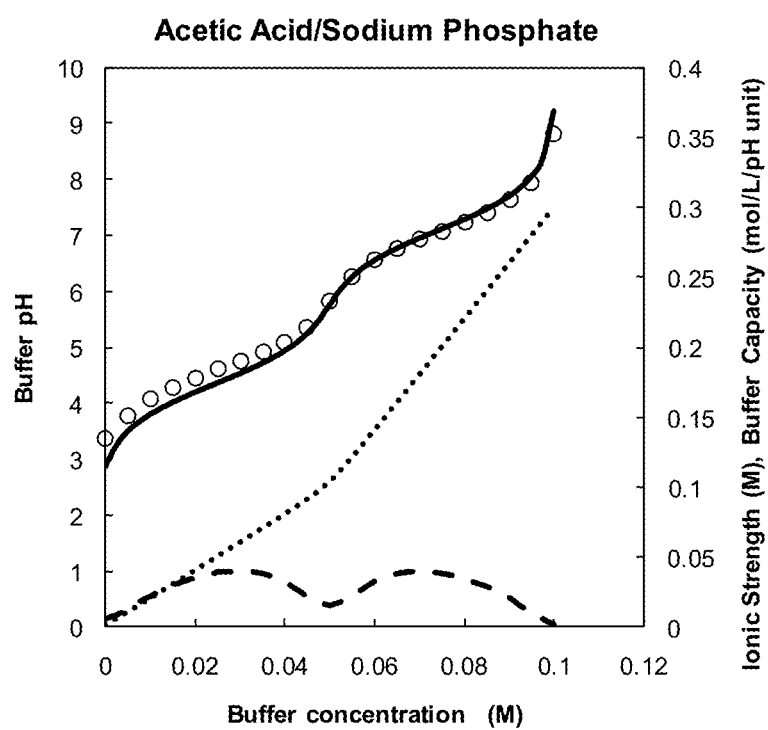
Figure 5. Calculated and experimental pH, ionic strength, and buffer capacity curves for acetic acid and sodium phosphate buffer system.

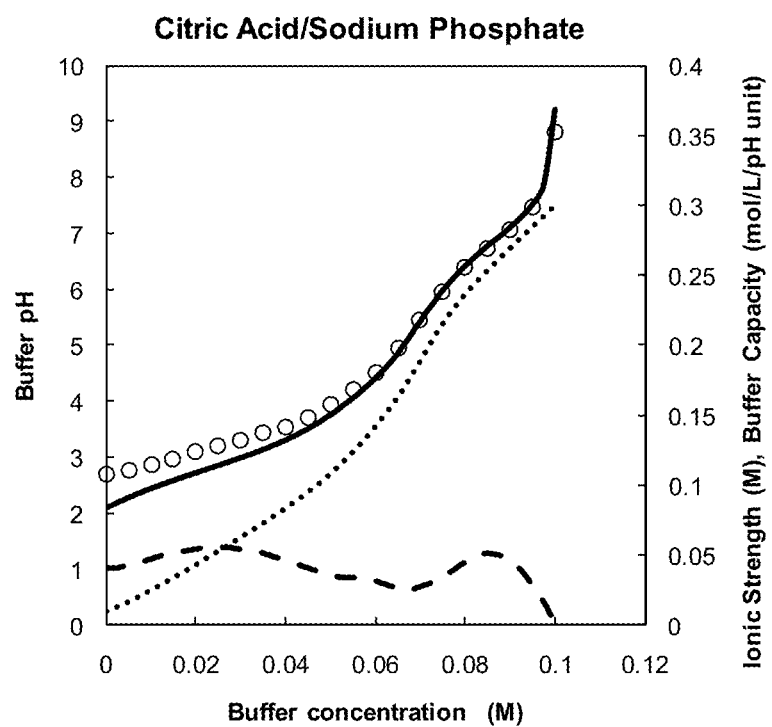
Figure 6. Calculated and experimental pH, ionic strength, and buffer capacity curves for citric acid and sodium phosphate buffer system.

BUFFER SYSTEM FOR PROTEIN PURIFICATION

This application is a Continuation of U.S. application Ser. No. 14/007,689, filed on 26 Sep. 2013, now U.S. Pat. No. 9,624,261, granted on Apr. 18, 2017, which is a 371 of International Application PCT/US2012/031076, filed on 29 Mar. 2012, which claims priority from Provisional Application 61/468,814, filed on 29 Mar. 2011.

FIELD OF INVENTION

The present invention relates to the field of recombinant protein purification from cell culture or fermentation broth using a series of chromatography unit operations. More specifically, the invention relates to a sodium chloride-free buffer system used across a series of unit operations for protein purification; where an acid and a base component, along with a third sodium salt buffer component, are combined at set ratios to provide adequate pH and conductivity control for robust chromatography operation.

BACKGROUND OF THE INVENTION

Orthogonal purification processes for the recovery of recombinant proteins are well established in the bioprocessing industry and continue to evolve for improved throughput, impurity clearance, reduced cost of goods, reduced development time, scalability, etc. In recent years, platform approaches have matured significantly to where generic template processes that require minimum development effort can be employed in the recovery of a variety of subclasses of recombinant proteins, especially monoclonal antibodies. In this case, the core concept underlying platform process development for monoclonal antibodies and other proteins is the identification and implementation of common unit operations that are applicable to wide class of target molecules, leading to a framework of purification steps that could be used to quickly design scalable, robust processes. As operating conditions for the sequence of chromatography and membrane/filtrations steps are developed, a key consideration is the careful selection of buffer components that lead to robustness and enhanced process performance. Without a systematic approach, the buffer selection process through traditional bench-scale experimentation can often lead to a large number of components that are not necessarily integrated from unit operation to unit operation and may be cumbersome to implement in large-scale manufacturing. To overcome these issues and limit the number of buffer components needed for an integrated process, we propose herein a sodium chloride-free two-component buffer system.

SUMMARY OF THE INVENTION

In one aspect the present invention is directed to a multi-component buffer system for the purification of proteins by a series of chromatography steps, where the modes of chromatography are selected from the group consisting of protein A chromatography, anion exchange chromatography, cation exchange chromatography, and mixed-mode chromatography, wherein the modes of chromatography are operated in either bind-elute mode or flow-through mode, where the multi-component buffer system comprises an organic acid, an alkaline metal or ammonium salt of the conjugate base of the organic acid, and an organic base and wherein the modes of chromatography are performed using buffers that are made without the addition of NaCl.

In another aspect, the present invention is directed to a method for purifying a protein from a contaminated solution thereof by Protein A chromatography comprising: (a) equilibrating a Protein A immobilized on a solid phase with a Protein A equilibration buffer comprising 55 mM tris base, 45 mM acetic acid, at about pH 7.5; (b) adsorbing the protein from the contaminated solution to the Protein A immobilized on the solid phase; (c) removing contaminants by washing the solid phase with a first Protein A wash buffer comprising 55 mM Tris Base, 45 mM Acetic acid, 300 mM Sodium Acetate, at about pH 7.5; and (d) recovering the protein from the solid phase with a Protein A elution buffer comprising 1.8 mM Sodium Acetate, 28.2 mM Acetic acid, at about pH 3.6, wherein all the buffers are made without the addition of NaCl.

In another aspect, the present invention is directed to a method for purifying a protein from a contaminated solution thereof by flowthrough anion exchange chromatography comprising: (a) equilibrating an anion exchange matrix with an anion equilibration buffer comprising 55 mM tris base, 45 mM acetic acid, at about pH 7.5; (b) applying the contaminated solution to the anion exchange matrix and collecting the first flowthrough; and (c) applying an anion wash buffer comprising 55 mM Tris Base, 45 mM Acetic acid, 300 mM Sodium Acetate, at about pH 7.5 to the anion exchange matrix and collecting the second flowthrough, wherein all the buffers are made without the addition of NaCl.

In another aspect, the present invention is directed to a method for purifying a protein from a contaminated solution thereof by cation exchange chromatography comprising: (a) equilibrating a cation exchange matrix with a cation equilibration buffer comprising 25 mM sodium acetate, 12.1 mM acetic acid, at about pH 5.0; (b) adsorbing the protein from the contaminated solution to the cation exchange matrix; (c) removing contaminants by washing the solid phase with a first cation wash buffer comprising 25 mM sodium acetate, 12.1 mM acetic acid, at about pH 5.0; and (d) recovering the protein from the solid phase with a cation elution buffer comprising 175 mM sodium acetate, 75 mM acetic acid, at about pH 5.0, wherein all the buffers are made without the addition of NaCl. The elimination of sodium chloride from the process ensures that the corrosive impact of high concentration chloride solutions on stainless steel processing equipment is managed and avoided all together.

BRIEF DESCRIPTION OF THE DRAWINGS

FIG. 1. Downstream process flow diagram for mAb platform. Key pH and ionic strength ranges for process chromatography control are shown.

FIG. 2. Diagram of ideal large scale buffer prep from concentrates for minimization of raw materials and tank requirements.

FIG. 3. Calculated and experimental pH, ionic strength, and buffer capacity curves for acetic acid and tris base buffer system.

FIG. 4. Calculated and experimental pH, ionic strength, and buffer capacity curves for citric acid and tris base buffer system.

FIG. 5. Calculated and experimental pH, ionic strength, and buffer capacity curves for acetic acid and sodium phosphate buffer system.

FIG. 6. Calculated and experimental pH, ionic strength, and buffer capacity curves for citric acid and sodium phosphate buffer system.

DETAILED DESCRIPTION OF THE INVENTION

It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a polypeptide" includes a combination of two or more polypeptides, and the like.

"About" as used herein when referring to a measurable value such as an amount, a temporal duration, and the like, is meant to encompass variations of ±20% or ±10%, including ±5%, ±1%, and ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

The benefits of a sodium chloride-free two-component buffer system may be realized with a wide variety of buffer components suitable for bioprocessing, for example, acetic acid and tris base. However, this specific pair of components, along with the third sodium salt conjugate base (e.g., sodium acetate), offers advantages for a monoclonal antibody platform that, in particular, incorporates anion- and cation-exchange chromatography as post capture polishing steps. In protein A chromatography these buffer species are especially suitable; where equilibration, loading, wash is normally performed at neutral pH and elution requires a step change to low pH. Here an acetic acid/tris mixture can be designed to buffer at pH 7.0-8.0 for equilibration, an acetic acid/sodium acetate/tris base mixture for wash at this same pH using high concentration sodium acetate increase ionic strength for optimal process- and product-related impurity clearance, and an acetic acid/sodium acetate mixture for elution at low pH (3.6-3.8). One other advantage is simply related to minimal electrostatic adsorption or exchange of acetate and tris buffer species during the relevant ion-exchange chromatographic operation. More specifically, because the tris base ion will possess a positive charge at neutral pH (where anion exchange chromatography for a typical antibody with high iso-electric point is commonly performed), it will mostly remain in solution throughout the AEX flow-through step providing adequate liquid-phase buffering at low ionic strength. Conversely, the acetate ion will possess a negative charge and will remain in solution through cation-exchange chromatography, again avoiding the exchange of buffer co-ions and providing buffering at an acidic pH (pH 5.0 for example). This approach at moderate buffer concentrations helps in maintaining constant pH through step changes, avoiding pH transients that can lead to a loss in impurity clearance and step performance [1], [2], [3]. Another key advantage is related to the single pKa values of these species and the buffer capacities at pH values that are most relevant for each step in the platform process (FIG. 1). The single pKa of the acetate buffer, for example, allows for reduced amount of strong acid and base that is needed to achieve target low pH or neutralization during the virus inactivation step, minimizing the increase in ionic strength that results through addition. Minimization of ionic strength during this step is critical for maximum performance of the following anion-exchange chromatography flow-through step. Low ionic strength in the anion-exchange product then enables high binding capacity in the cation-exchange chromatography step, fully integrating all four steps in the process (from a buffer selection point of view) and avoiding the need for TFUF or dilution between steps. Finally, the elimination of sodium chloride from the process ensures that the corrosive impact of high concentration chloride solutions on stainless steel processing equipment is managed and avoided all together. High concentration chloride solution, especially at acidic pH levels (needed for example during cation-exchange chromatography), are associated with corrosion and have been reported as problematic to manufacturing facilities [4].

The present invention specifically relates to the use the simplified acid/base buffer system in the context of a platform process in combination with sodium salt buffer component as a replacement for sodium chloride, high concentration tris base, or other component for ionic strength modulation. This approach leads to more robust pH and conductivity control across the 3.4-7.7 pH range, and in turn, improves the performance of each chromatography step, relative to a more traditional process that incorporates a greater number of buffer components.

"Polypeptide," "peptide" and "protein" are used interchangeably herein to refer to a polymer of amino acid residues. A polypeptide can be of natural (tissue-derived) origins, recombinant or natural expression from prokaryotic or eukaryotic cellular preparations, or produced chemically via synthetic methods. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but that functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine: D-(trifluoromethyl)-phenylglycine; D-(trifluoromethyl)-phenylalanine: D-p-fluorophenylalanine; D- or L-p-biphenylphenylalanine; K- or L-p-methoxy-biphenylphenylalanine: D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Peptide" as used herein includes peptides which are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. "Conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. "Cationic" as used herein refers to any peptide that possesses a net positive charge at pH 7.4. The biological activity of the peptides can be determined by standard methods known to those of skill in the art and described herein.

"Recombinant", when used with reference to a protein, indicates that the protein has been modified by the introduction of a heterologous nucleic acid or protein or the alteration of a native nucleic acid or protein.

As used herein, a "therapeutic protein", refers to any protein and/or polypeptide that can be administered to a mammal to elicit a biological or medical response of a tissue, system, animal or human that is being sought, for instance, by a researcher or clinician. A therapeutic protein may elicit more than one biological or medical response. Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function, as well as amounts effective to cause a physiological function in a patient which enhances or aids in the therapeutic effect of a second pharmaceutical agent.

All "amino acid" residues identified herein are in the natural L-configuration. In keeping with standard polypeptide nomenclature, abbreviations for amino acid residues are as shown in the following table.

TABLE 1

Amino acid abbreviations.

| 1 Letter | 3 Letter | Amino Acid |
|---|---|---|
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | leucine |
| T | Thr | L-threonine |
| V | Val | L-valine |
| P | Pro | L-proline |
| K | Lys | L-lysine |
| H | His | L-histidine |

TABLE 1-continued

Amino acid abbreviations.

| 1 Letter | 3 Letter | Amino Acid |
|---|---|---|
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine. |

It should be noted that all amino acid residue sequences are represented herein by formulae whose left to right orientation is in the conventional direction of amino-terminus to carboxy-terminus.

In another embodiment, the polypeptide is an antigen binding polypeptide. In one embodiment, the antigen binding polypeptide is selected from the group consisting of a soluble receptor, antibody, antibody fragment, immunoglobulin single variable domain, Fab, F(ab')2, Fv, disulphide linked Fv, scFv, closed conformation multispecific antibody, disulphide-linked scFv, or diabody.

The term "antigen binding polypeptide", as used herein, refers to antibodies, antibody fragments and other protein constructs which are capable of binding to an antigen.

The terms, Fv, Fc, Fd, Fab, or F(ab)2, are used with their standard meanings (see, e.g., Harlow et al., Antibodies A Laboratory Manual, Cold Spring Harbor Laboratory, (1988)).

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see, for example, EP-A-0239400 and EP-A-054951.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs", as used herein, refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See, for example, Chothia et al., (1989) Conformations of immunoglobulin hypervariable regions; Nature 342, p 877-883.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species, such as rodent (for example, as disclosed in WO 00/29004), nurse shark and Camelid $V_{HH}$ dAbs (nanobodies). Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are still considered to be "domain antibodies" according to the invention. As used herein "$V_H$ includes camelid $V_{HH}$ domains. NARV are another type of immunoglobulin single variable domain which were identified in cartilaginous fish including the nurse shark. These domains are also known as Novel Antigen Receptor variable region (commonly abbreviated to V(NAR) or NARV). For further details, see Mol. Immunol. 44, 656-665 (2006) and US20050043519A.

The term "Epitope-binding domain" refers to a domain that specifically binds an antigen or epitope independently of a different V region or domain, this may be a domain antibody (dAb), for example a human, camelid or shark immunoglobulin single variable domain.

As used herein, the term "antigen-binding site" refers to a site on a protein which is capable of specifically binding to antigen, this may be a single domain, for example an epitope-binding domain, or it may be paired $V_H/V_L$ domains as can be found on a standard antibody. In some aspects of the invention single-chain Fv (ScFv) domains can provide antigen-binding sites.

The terms "mAbdAb" and "dAbmAb" are used herein to refer to antigen-binding proteins of the present invention. The two terms can be used interchangeably, and are intended to have the same meaning as used herein.

In one aspect, the present invention is directed to a multi-component buffer system for the purification of proteins by a series of chromatography steps, where the modes of chromatography are selected from the group consisting of affinity chromatography, anion exchange chromatography, cation exchange chromatography, and mixed-mode chromatography, wherein the modes of chromatography are operated in either bind-elute mode or flowthrough mode, where the multi-component buffer system comprises an organic acid, an alkaline metal or ammonium salt of the conjugate base of the organic acid, and an organic base and wherein the modes of chromatography are performed using buffers that are made without the addition of NaCl.

In one embodiment, the affinity chromatography is performed using a superantigen. "Superantigen" refers to generic ligands that interact with members of the immunoglobulin superfamily at a site that is distinct from the target ligand-binding sites of these proteins. Staphylococcal enterotoxins are examples of superantigens which interact with T-cell receptors. Superantigens that bind antibodies include, but are not limited to, Protein G, which binds the IgG constant region (Bjorck and Kronvall, J. Immunol., 133:969 (1984)); Protein A which binds the IgG constant region and $V_H$ domains (Forsgren and Sjoquist, J. Immunol., 97:822 (1966)); and Protein L which binds $V_L$ domains (Bjorck, J. Immunol., 140:1194 (1988)). In one embodiment the superantigen is Protein A.

In many cases, it may be more advantageous to actually select conditions at which the protein will flow through while the contaminants will bind. This mode of binding is often referred to as "flowthrough mode". In the present application, solution which flows through during chromatography is referred to as "flowthrough".

When used herein, the term "Protein A" encompasses Protein A recovered from a native source thereof, Protein A produced synthetically (e.g., by peptide synthesis or by recombinant techniques), and variants thereof which retain the ability to bind proteins which have a $C_H2/C_H3$ region. Protein A can be purchased commercially from Repligen, Pharmacia and Fermatech.

The superantigen is immobilized on a solid phase. By "solid phase" is meant a non-aqueous matrix to which the superantigen can adhere. The solid phase of interest herein is generally one which comprises a glass, silica, agarose or polystyrene surface. The solid phase may be a purification column or a discontinuous phase of discrete particles. In preferred embodiments, the solid phase is a controlled pore glass column or a silicic acid column. In certain embodiments, the solid phase is coated with a reagent (such as glycerol), which is intended to prevent nonspecific adherence of contaminants to the solid phase.

A "buffer" is a buffered solution that resists changes in pH by the action of its acid-base conjugate components.

An "equilibration buffer" herein is that used to prepare the solid phase for chromatography.

The "loading buffer" is that which is used to load the mixture of the protein and contaminant(s) onto the chromatography matrix. The equilibration and loading buffers can be the same.

The "elution buffer" is used to elute proteins from the chromatography matrix.

A "salt" is a compound formed by the interaction of an acid and a base.

In one embodiment, the organic acid includes, but is not limited to, formic acid, acetic acid, lactic acid, citric acid, malic acid, maleic acid, glycine, phosphoric acid, glycylclycine, succinic acid, TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

In one embodiment, the organic base includes, but is not limited to, the group consisting of tris base, arginine, Bis-Tris, Bis-Tris-Propane, Bicine (N,N-bis(2-hydroxyethyl)glycine), HEPES (4-2-hydroxyethyl-1-piperazineethanesulfonic acid), TAPS (3-{[tris(hydroxymethyl)methyl]amino}propanesulfonic acid), and Tricine (N-tris(hydroxymethyl)methylglycine).

In one embodiment, the conjugate base of the organic acid is the sodium, potassium, or ammonium salt of the conjugate base of the organic acid. In one embodiment, the organic acid is acetic acid and the conjugate base of acetic acid is the sodium salt.

In one embodiment, the protein is an antigen binding protein. In one embodiment, the antigen binding protein is an antibody. In one embodiment the antibody is of the IgG class. In one embodiment, the antigen binding protein is a immunoglobulin single variable domain.

In one embodiment, the sequence of chromatographic steps comprises protein A chromatography and flowthrough anion exchange chromatography. In one embodiment, the sequence of chromatographic steps comprises protein A chromatography, flowthrough anion exchange chromatography, and cation exchange chromatography.

In one embodiment, the sequence of chromatographic steps comprises protein A chromatography performed in the presence of about 55 mM tris base, about 45 mM acetic acid, at about pH 7.5.

In one embodiment, the sequence of chromatographic steps comprises flowthrough anion exchange chromatography performed in the presence of about 55 mM tris base, about 45 mM acetic acid, at about pH 7.5.

In one embodiment, the sequence of chromatographic steps comprises cation exchange chromatography performed in the presence of about 25 mM sodium acetate, about 12.1 mM acetic acid, at about pH 5.0.

In one aspect, the present invention is directed to a method for purifying a protein from a contaminated solution thereof by Protein A chromatography comprising: (a) equilibrating a Protein A immobilized on a solid phase with a Protein A equilibration buffer comprising about 55 mM tris base, about 45 mM acetic acid, at about pH 7.5; (b) adsorbing the protein from the contaminated solution to the Protein A immobilized on the solid phase; (c) removing contaminants by washing the solid phase with a first Protein A wash buffer comprising about 55 mM Tris Base, about 45 mM Acetic acid, 300 mM Sodium Acetate, at about pH 7.5; and (d) recovering the protein from the solid phase with a Protein A elution buffer comprising about 1.8 mM Sodium Acetate, about 28.2 mM Acetic acid, at about pH 3.6, wherein all the buffers are made without the addition of NaCl.

In one embodiment, the method further comprises the following step after step (c) and before step (d): removing contaminants by washing the solid phase with a second Protein A wash buffer comprising about 55 mM Tris Base, about 45 mM Acetic acid, at about pH 7.5, wherein the second Protein A wash buffer is made without the addition of NaCl.

In one embodiment, the method further comprises the following steps after step (d): (e) titrating the solution containing the recovered protein to about pH 3.0 with about 30 mM acetic acid, about 100 mM HCl; (f) allowing the solution of step (e) to remain at about pH 3.0 for about 30 to about 60 minutes; and (g) adjusting the pH of the solution of step (f) to about pH 7.5 with about 1 M Tris.

In one embodiment, the method further comprises filtering the solution produced by step (g) above.

In one aspect the present invention is directed to a method for purifying a protein from a contaminated solution thereof by flowthrough anion exchange chromatography comprising: (a) equilibrating an anion exchange matrix with an anion equilibration buffer comprising about 55 mM tris base, about 45 mM acetic acid, at about pH 7.5; (b) applying the contaminated solution to the anion exchange matrix and collecting the first flowthrough; and (c) applying an anion wash buffer comprising 55 mM Tris Base, about 45 mM Acetic acid, about 300 mM Sodium Acetate, at about pH 7.5 to the anion exchange matrix and collecting the second flowthrough, wherein all the buffers are made without the addition of NaCl.

In one embodiment, the contaminated solution is the solution produced by step (g) of a method for purifying a protein from a contaminated solution thereof by Protein A chromatography comprising: (a) equilibrating a Protein A immobilized on a solid phase with a Protein A equilibration buffer comprising 55 mM tris base, 45 mM acetic acid, at about pH 7.5; (b) adsorbing the protein from the contaminated solution to the Protein A immobilized on the solid phase; (c) removing contaminants by washing the solid phase with a first Protein A wash buffer comprising 55 mM Tris Base, 45 mM Acetic acid, 300 mM Sodium Acetate, at about pH 7.5; and (d) recovering the protein from the solid phase with a Protein A elution buffer comprising 1.8 mM Sodium Acetate, 28.2 mM Acetic acid, at about pH 3.6, wherein all the buffers are made without the addition of NaCl. or the filtered solution of a method of purifying a protein from a contaminated solution thereof by Protein A chromatography comprising: (a) equilibrating a Protein A immobilized on a solid phase with a Protein A equilibration buffer comprising 55 mM tris base, 45 mM acetic acid, at about pH 7.5; (b) adsorbing the protein from the contaminated solution to the Protein A immobilized on the solid phase; (c) removing contaminants by washing the solid phase with a first Protein A wash buffer comprising 55 mM Tris Base, 45 mM Acetic acid, 300 mM Sodium Acetate, at about pH 7.5; and (d) recovering the protein from the solid phase with a Protein A elution buffer comprising 1.8 mM Sodium Acetate, 28.2 mM Acetic acid, at about pH 3.6, wherein all the buffers are made without the addition of NaCl, further comprising the following step after step (c) and before step (d): removing contaminants by washing the solid phase with a second Protein A wash buffer comprising 55 mM Tris Base, 45 mM Acetic acid, at about pH 7.5, wherein the second Protein A wash buffer is made without the addition of NaCl.

In one embodiment, the first flowthrough and the second flowthrough are combined into a single combined flowthrough solution.

In one embodiment, the pH of the first flowthrough, the second flowthrough, and the single combined flowthrough solution is adjust to about pH 5.0 with 30 mM acetic acid, 100 mM HCl.

In one aspect, the present invention is directed to a method for purifying a protein from a contaminated solution thereof by cation exchange chromatography comprising: (a) equilibrating a cation exchange matrix with a cation equilibration buffer comprising about 25 mM sodium acetate, about 12.1 mM acetic acid, at about pH 5.0; (b) adsorbing the protein from the contaminated solution to the cation exchange matrix; (c) removing contaminants by washing the solid phase with a first cation wash buffer comprising about 25 mM sodium acetate, about 12.1 mM acetic acid, at about pH 5.0; and (d) recovering the protein from the solid phase with a cation elution buffer comprising 175 mM sodium acetate, 75 mM acetic acid, at about pH 5.0, wherein all the buffers are made without the addition of NaCl.

In one embodiment, the contaminated solution is selected from the first flowthrough of a method of purifying a protein from a contaminated solution thereof by Protein A chromatography comprising: (a) equilibrating a Protein A immobilized on a solid phase with a Protein A equilibration buffer comprising 55 mM tris base, 45 mM acetic acid, at about pH 7.5; (b) adsorbing the protein from the contaminated solution to the Protein A immobilized on the solid phase; (c) removing contaminants by washing the solid phase with a first Protein A wash buffer comprising 55 mM Tris Base, 45 mM Acetic acid, 300 mM Sodium Acetate, at about pH 7.5; and (d) recovering the protein from the solid phase with a Protein A elution buffer comprising 1.8 mM Sodium Acetate, 28.2 mM Acetic acid, at about pH 3.6, wherein all the buffers are made without the addition of NaCl., further comprising the following steps after step (d): (e) titrating the solution containing the recovered protein to about pH 3.0 with 30 mM acetic acid, 100 mM HCl; (f) allowing the solution of step (e) to remain at about pH 3.0 for about 30 to about 60 minutes; (g) adjusting the pH of the solution of step (f) to about pH 7.5 with 1 M Tris or a method of further comprising the following steps after step (d): (e) titrating the solution containing the recovered protein to about pH 3.0 with 30 mM acetic acid, 100 mM HCl; (f) allowing the solution of step (e) to remain at about pH 3.0 for about 30 to about 60 minutes; (g) adjusting the pH of the solution of step (f) to about pH 7.5 with 1 M Tris further comprising filtering the solution produced by step (g), the second flowthrough of a method of purifying a protein from a contaminated solution thereof by Protein A chromatography comprising: (a) equilibrating a Protein A immobilized on a solid phase with a Protein A equilibration buffer comprising 55 mM tris base, 45 mM acetic acid, at about pH 7.5; (b) adsorbing the protein from the contaminated solution to the Protein A immobilized on the solid phase; (c) removing contaminants by washing the solid phase with a first Protein A wash buffer comprising 55 mM Tris Base, 45 mM Acetic acid, 300 mM Sodium Acetate, at about pH 7.5; and (d) recovering the protein from the solid phase with a Protein A elution buffer comprising 1.8 mM Sodium Acetate, 28.2 mM Acetic acid, at about pH 3.6, wherein all the buffers are made without the addition of NaCl, further comprising the following steps after step (d): (e) titrating the solution containing the recovered protein to about pH 3.0 with 30 mM acetic acid, 100 mM HCl; (f) allowing the solution of step (e) to remain at about pH 3.0 for about 30 to about 60 minutes; (g) adjusting the pH of the solution of step (f) to about pH 7.5 with 1 M Tris or a method of further comprising the following steps after step (d): (e) titrating the solution containing the recovered protein to about pH 3.0 with 30 mM acetic acid, 100 mM HCl; (f) allowing the solution of step (e) to remain at about pH 3.0 for about 30 to about 60 minutes; (g) adjusting the pH of the solution of step (f) to about pH 7.5 with 1 M Tris further comprising filtering the solution produced by step (g), the single flowthrough combined solution of a method for purifying a protein from a contaminated solution thereof by flowthrough anion exchange chromatography comprising: (a) equilibrating an anion exchange matrix with an anion equilibration buffer comprising 55 mM tris base, 45 mM acetic acid, at about pH 7.5; (b) applying the contaminated solution to the anion exchange matrix and collecting the first flowthrough; and (c) applying an anion wash buffer comprising 55 mM Tris Base, 45 mM Acetic acid, 300 mM Sodium Acetate, at about pH 7.5 to the anion exchange matrix and collecting the second flowthrough, wherein all the buffers are made without the addition of NaCl, and the pH-adjusted flowthrough produced by a method of a method for purifying a protein from a contaminated solution thereof by flowthrough anion exchange chromatography comprising: (a) equilibrating an anion exchange matrix with an anion equilibration buffer comprising 55 mM tris base, 45 mM acetic acid, at about pH 7.5; (b) applying the contaminated solution to the anion exchange matrix and collecting the first flowthrough; and (c) applying an anion wash buffer comprising 55 mM Tris Base, 45 mM Acetic acid, 300 mM Sodium Acetate, at about pH 7.5 to the anion exchange matrix and collecting the second flowthrough, wherein all the buffers are made without the addition of NaCl wherein the contaminated solution is the solution produced by step (g) of a method for purifying a protein from a contaminated solution thereof by Protein A chromatography comprising: (a) equilibrating a Protein A immobilized on a solid phase with a Protein A equilibration buffer comprising 55 mM tris base, 45 mM acetic acid, at about pH 7.5; (b) adsorbing the protein from the contaminated solution to the Protein A immobilized on the solid phase; (c) removing contaminants by washing the solid phase with a first Protein A wash buffer comprising 55 mM Tris Base, 45 mM Acetic acid, 300 mM Sodium Acetate, at about pH 7.5; and (d) recovering the protein from the solid phase with a Protein A elution buffer comprising 1.8 mM Sodium Acetate, 28.2 mM Acetic acid, at about pH 3.6, wherein all the buffers are made without the addition of NaCl or the filtered solution of the method of purifying a protein from a contaminated solution thereof by Protein A chromatography comprising: (a) equilibrating a Protein A immobilized on a solid phase with a Protein A equilibration buffer comprising 55 mM tris base, 45 mM acetic acid, at about pH 7.5; (b) adsorbing the protein from the contaminated solution to the Protein A immobilized on the solid phase; (c) removing contaminants by washing the solid phase with a first Protein A wash buffer comprising 55 mM Tris Base, 45 mM Acetic acid, 300 mM Sodium Acetate, at about pH 7.5; and (d) recovering the protein from the solid phase with a Protein A elution buffer comprising 1.8 mM Sodium Acetate, 28.2 mM Acetic acid, at about pH 3.6, wherein all the buffers are made without the addition of NaCl, further comprising the following step after step (c) and before step (d): removing contaminants by washing the solid phase with a second Protein A wash buffer comprising 55 mM Tris Base, 45 mM Acetic acid, at about pH 7.5, wherein the second Protein A wash buffer is made without the addition of NaCl.

Example 1

A number of potential buffer components that could be implemented in a two-component buffer system, along with a third component for modulating ionic strength (deliberately excluding sodium chloride) through a platform process for antibody purification have been evaluated. Table 2 lists these components that are generally considered compatible with bioprocesses. In these experiments, as shown in FIG. 2, a liquid chromatography system with gradient delivery capabilities, was used to mix concentrated buffer solutions and measure pH and conductivity at various ratios. FIGS. 3, 4, 5, and 6 present sample results for acetic acid/tris base, citric acid/tris base, acetic acid/sodium phosphate, and citric acid/sodium phosphate, respectively. In these figures, open circle data points represent experimentally measured pH values as a function of buffer molarity, while solid and dashed lines represent calculated pH, conductivity (in general proportional to solution conductivity), and buffer capacity values determined through solution of the well-established Davies mathematical model [5] for predicting the behavior of ions in aqueous solutions. These curves allow the determination of the required buffer ratios needed to produce a mixture of ionic species that result in a specific pH and ionic strength level, and thus become a tool for evaluating the appropriateness of a buffer for a specific chromatography step.

TABLE 2

Buffers considered for two-component mixing studies.

| Buffer Component | Charge, Fully deprotonated | pKa1 | pKa2 | pKa3 |
|---|---|---|---|---|
| Acetic Acid | −1 | 4.757 | — | — |
| Citric Acid | −3 | 3.128 | 4.761 | 6.396 |
| Tris | 0 | 8.075 | — | — |
| Phosphoric Acid | −3 | 2.148 | 7.199 | 12.35 |
| Glycine | −2 | 2.35 | 9.778 | — |
| Arginine | −1 | 1.823 | 8.991 | 12.48 |
| Bis-Tris | 0 | 6.46 | — | — |
| Bis-Tris Propane | 0 | 6.80 | 9.0 | — |
| Malic Acid | −2 | 3.459 | 5.097 | — |
| HEPES | −1 | ~3 | 7.48 | — |

For example, FIG. 3 shows these results for an acetic acid and tris base mixture, demonstrating that in order to buffer, for example, at pH 7.5, a composition of 55 mM tris Base, 45 mM acetic acid is needed and provides a capacity of 19 mM. Generally, buffers are considered "adequate" buffers when buffering capacity approaches 20 mM. Other combinations of the various components shown in Table 2 may be assessed in this manner and then tested in chromatographic experiments.

This approach was applied to further determine the composition of acetic acid and tris base that would be needed to meet the desired pH and conductivity ranges for the overall platform process shown in FIG. 1. A range of pH values is specifically needed for each chromatography unit operation in the platform ranging from 3.6 to 7.5 pH units, along with a range of conductivity levels from low to high. This latter requirement (conductivity control) can be accomplished with various components. In this example, sodium acetate was selected as the conjugate base to acetic acid used to increase the ionic strength of the buffer, where the sodium ion provides a direct increase in ionic strength. Table 3 summarizes the final buffer compositions of this two-component buffer system to be used in purification experiments. In this table, note the use of high concentration sodium acetate in the protein A wash and cation-exchange chromatography elution steps and the absence of sodium chloride.

TABLE 3

Acetic acid, sodium acetate, and tris base buffer system and other solutions used in each step of the antibody platform.

| Protein A Chromatography | |
|---|---|
| Equilibration | 55 mM Tris Base, 45 mM Acetic acid, pH 7.5 ± 0.2 |
| Load | Clarified Cell Culture fluid |
| Wash 1 | 55 mM Tris Base, 45 mM Acetic acid, 300 mM Sodium Acetate, pH 7.5 ± 0.2 |
| Wash 2 | 55 mM Tris Base, 45 mM Acetic acid, pH 7.5 ± 0.2 |
| Elution | 1.8 mM Sodium Acetate, 28.2 mM Acetic acid, pH 3.6 ± 0.1 |
| Strip | 300 mM Acetic Acid, pH 2.6 ± 0.2 |
| Clean | 0.1M Sodium Hydroxide |
| Store | 2% Benzyl Alcohol or 18% Ethanol (or other) |
| Low pH Inactivation | |
| Low pH Adjustment Buffer | Protein A Eluate titrated to pH 3.5 with 30 mM Acetic Acid, 100 mM HCl |
| Inactivation Hold | ≥30 minute hold not to exceed 60 minutes |
| Post-Hold pH Adjustment | Low pH treated product pH adjusted to pH 7.5 with 1M Tris Base |
| Anion-Exchange Chromatography | |
| Pre-Equilibration | Water for injection (WFI) |
| Equilibration | 55 mM Tris Base, 45 mM Acetic acid, pH 7.5 ± 0.2 |
| Load | pH Adjusted Low pH treated product |
| Wash 1 | 55 mM Tris Base, 45 mM Acetic acid, pH 7.5 ± 0.2 |
| Clean | 1.0M Sodium Hydroxide |
| Store | 0.1M Sodium Hydroxide |
| Cation-Exchange Chromatography | |
| Equilibration | 25 mM Sodium Acetate, 12.1 mM Acetic acid, pH 5.0 ± 0.2 |
| Load | pH 5.0 ± 0.10 adjusted anion-exchange product; |
| Wash 1 | 25 mM Sodium Acetate, 12.1 mM Acetic acid, pH 5.0 ± 0.2 |
| Elution | 175 mM Sodium Acetate, 75 mM acetic acid, pH 5.0 ± 0.2 |
| Clean | 1.0M Sodium Hydroxide |
| Store | 0.1M Sodium Hydroxide |

Example 2

All chromatographic processes are carried out using an AKTA Explorer 100 system from GE Healthcare (Piscataway, N.J., USA). MabSelect SuRe Protein A and CaptoQ chromatography media are obtained from GE Healthcare (Piscataway, N.J., USA). GigaCapS 650M cation exchange resin is obtained from Tosoh Bioscience (Montgomeryville, Pa., USA). Chromatography media is packed to a bed height of 25 cm, according to manufacturer's recommendation, in 1.1 cm diameter Vantage columns obtained from Millipore Corporation (Bedford, Mass., USA). The IgG monoclonal antibodies used for this work are recombinantly expressed using mammalian cell culture at the GlaxoSmithKline Upper Merion site (King of Prussia, Pa., USA). All chemicals are obtained from JT Baker (Phillipsburg, N.J., USA) or Sigma Aldrich (St Louis, Mo., USA) and are of USP grade.

Protein A Chromatography

Purification of monoclonal antibodies by Protein A affinity chromatography utilizing MabSelect SuRe are carried out according to Table 2. First, the column is equilibrated with 55 mM Tris Base, 45 mM Acetic acid, pH 7.5. Clarified mammalian cell culture broth is then applied to the column until sufficient load mass had been applied to the column. The column is then washed with 55 mM Tris Base, 45 mM Acetic acid, 300 mM Sodium Acetate, pH 7.5. Prior to elution, the column is re-equilibrated with 55 mM Tris Base, 45 mM Acetic Acid, pH 7.5. The column is then eluted with 1.8 mM Sodium Acetate, 28.2 mM Acetic Acid, pH 3.6.

Low pH Treatment for Virus Inactivation

Protein A Eluate from the previous step is adjusted to pH 3.5 with 30 mM Acetic Acid, 100 mM HCl. The low pH adjusted material is held for 30 to 60 minutes then neutralized to pH 7.5 with 1 M Tris Base. The neutralized pool is then filtered in preparation for subsequent purification steps.

Anion-Exchange Flow-Through Chromatography

Further purification is accomplished by equilibrating the CaptoQ column with 55 mM Tris Base, 45 mM Acetic Acid, pH 7.5 following a pre-equilibration rinse with WFI (water for injection). Note that the same equilibration buffer used for the protein A equilibration is re-used in this step, offering the advantage of minimizing buffer solutions that need to be prepared. The neutralized pool is then applied to the column where the protein of interest flowed through and is collected while the contaminants remained bound to the column. Following the application of protein, the column is then washed with adequate equilibration buffer such that the remaining protein is washed from the column and able to be collected.

Cation-Exchange Chromatography

Protein collected from the anion-exchange flow-through step is titrated to pH 5.0 with 30 mM Acetic Acid, 100 mM HCl. Again, note the re-use of the low pH treatment solution for pH adjustment in this step. The GigaCapS 650M column is equilibrated with 25 mM Sodium Acetate, 12.1 mM Acetic Acid, pH 5.0. The titrated load is then applied to the column until the desired load mass is achieved. The column is then re-equilibrated with 25 mM Sodium Acetate, 12.1 mM Acetic Acid, pH 5.0. Next the column is step eluted by applying to the column 175 mM Sodium Acetate, 75 mM Acetic Acid, pH 5.0. The column effluent is collected and retained for further processing.

REFERENCES

1. Ghose, S.; McNerney, T. M. Hubbard, B. pH transitions in ion-exchange systems: Role in the development of a cation exchange process for a recombinant protein. Biotechnol. Prog. 2002, 18, 530-537.
2. Soto Perez, J. and Frey, D. D. Behavior of the Inadvertent pH Transient Formed by a Salt Gradient in the Ion-Exchange Chromatography of Proteins, Biotechnol. Prog. 2005, 21, 902-910
3. Pabst, T. M., Carta, G. pH transitions in cation exchange chromatographic columns containing weak acid groups. (2007) Journal of Chromatography A, 1142, pp. 19-31.
4. Zhou, J. X., et al. pH-conductivity hybrid gradient cation-exchange chromatography for process-scale monoclonal antibody purification. Journal of Chromatography A, 1175 (2007) 69-80
5. Butler, J. N., Ionic Equilibrium: Solubility and pH Calculations. John Wiley and Sons (1998).

What is claimed:

1. A method for purifying a protein from a contaminated solution thereof comprising the steps of:
   (1) passing the protein through a series of chromatography steps operated in a mode chosen from: bind-elute mode and flow-through mode, using a sodium chloride-free multi-component buffer system,
       wherein the chromatography steps comprise affinity chromatography and at least one additional chromatography step chosen from: anion exchange chromatography, cation exchange chromatography, and mixed-mode chromatography, and
       wherein the sodium chloride-free multi-component buffer system comprises:
       (a) an organic acid,
       (b) at least one component chosen from an alkaline metal and an ammonium salt of the conjugate base of the organic acid of (a), and
       (c) an organic base; and
       wherein the sodium chloride-free multi-component buffer system is used throughout the series of chromatography steps; and
   (2) recovering the purified protein.

2. The method as claimed in claim 1, wherein each chromatography step comprises:
   (1) an equilibration step using an equilibration buffer solution,
   (2) a wash step using a wash buffer solution and, optionally,
   (3) an elution step using an elution buffer solution,
       wherein the equilibration buffer, wash buffer and elution buffer solutions are all made using the sodium chloride-free multi-component buffer system.

3. The method as claimed in claim 1, wherein the organic acid comprises acetic acid.

4. The method as claimed in claim 1, wherein the organic base is tris base.

5. The method as claimed in claim 1, wherein the alkaline metal or ammonium salt of the conjugate base of the organic acid is chosen from the sodium, potassium, and ammonium salt of the conjugate base of the organic acid.

6. The method as claimed in claim 1, wherein the organic acid is acetic acid, and the conjugate base of acetic acid is the sodium salt.

7. The method as claimed in claim 1, wherein the protein is an antigen binding protein.

8. The method as claimed in claim 7, wherein the antigen binding protein is an antibody of the IgG class.

9. The method as claimed in claim 7, wherein the antigen binding protein is an immunoglobulin single variable domain.

10. The method as claimed in claim 1, wherein the series of chromatography steps comprises affinity chromatography and anion exchange chromatography, optionally followed by cation exchange chromatography.

11. The method as claimed in claim 1, wherein the affinity chromatography comprises Protein A chromatography.

12. The method as claimed in claim 11, wherein the affinity chromatography comprises Protein A chromatography performed in the presence of tris base and acetic acid, at about pH 7.5.

13. The method as claimed in claim 1, wherein the series of chromatography steps comprises anion exchange chromatography performed in the presence of tris base and acetic acid, at about pH 7.5.

14. The method as claimed in claim 1, wherein the series of chromatography steps comprises cation exchange chromatography performed in the presence of sodium acetate and acetic acid, at about pH 5.0.

15. The method as claimed in claim 1, wherein the affinity chromatography steps comprise:
  (a) equilibrating a Protein A immobilized on a solid phase with a Protein A equilibration buffer solution;
  (b) adsorbing the protein from the contaminated solution to the Protein A immobilized on the solid phase;
  (c) removing contaminants by washing the solid phase with a Protein A wash buffer solution; and
  (d) recovering the protein from the solid phase with a Protein A elution buffer solution,
  wherein all of the buffer solutions are made using the sodium chloride-free multi-component buffer system.

16. The method as claimed in claim 1, wherein the affinity chromatography is followed by anion exchange chromatography comprising the steps of:
  (a) equilibrating an anion exchange matrix with an anion exchange equilibration buffer solution;
  (b) applying the contaminated solution to the anion exchange matrix and collecting the first flowthrough; and
  (c) applying an anion exchange wash buffer solution to the anion exchange matrix and collecting the second flowthrough,
  wherein all of the buffer solutions are made using the sodium chloride-free multi-component buffer system.

17. The method as claimed in claim 16, wherein the first flowthrough and the second flowthrough are combined into a single flowthrough solution.

18. The method as claimed in claim 1, wherein the affinity chromatography is followed by cation exchange chromatography comprising the steps of:
  (a) equilibrating a cation exchange matrix with a cation exchange equilibration buffer solution;
  (b) adsorbing the protein from the contaminated solution to the cation exchange matrix;
  (c) removing contaminants by washing the solid phase with a first cation exchange wash buffer solution; and
  (d) recovering the protein from the solid phase with a cation exchange elution buffer solution,
  wherein all the buffer solutions are made using the sodium chloride-free multi-component buffer system.

* * * * *